US 11,376,018 B2

(12) United States Patent
Lee

(10) Patent No.: US 11,376,018 B2
(45) Date of Patent: Jul. 5, 2022

(54) ADJUSTABLE REVISION GUIDE WITH TRANSLATING STEM ADAPTOR

(71) Applicant: MicroPort Orthopedic Holdings Inc., Arlington, TN (US)

(72) Inventor: Daniel Lee, Memphis, TN (US)

(73) Assignee: MicroPort Orthopedics Holdings Inc., Arlington, TN (US)

( * ) Notice: Subject to any disclaimer, the term of this patent is extended or adjusted under 35 U.S.C. 154(b) by 179 days.

(21) Appl. No.: 17/020,600

(22) Filed: Sep. 14, 2020

(65) Prior Publication Data

US 2021/0128173 A1 May 6, 2021

Related U.S. Application Data

(60) Provisional application No. 62/900,499, filed on Sep. 14, 2019.

(51) Int. Cl.
*A61B 17/15* (2006.01)
*A61B 17/00* (2006.01)

(52) U.S. Cl.
CPC .. *A61B 17/155* (2013.01); *A61B 2017/00367* (2013.01)

(58) Field of Classification Search
CPC ........ A61B 17/155; A61B 2017/00367; A61B 17/157; A61B 17/1764; A61F 2/4657; A61F 2/3859; A61F 2/4684; A61F 2002/4658
See application file for complete search history.

(56) References Cited

U.S. PATENT DOCUMENTS

| | | |
|---|---|---|
| 5,053,037 A | 10/1991 | Lackey |
| 5,879,393 A | 3/1999 | Whiteside et al. |
| 6,187,010 B1 | 2/2001 | Masini |
| 6,575,980 B1 | 6/2003 | Robie et al. |
| RE39,301 E | 9/2006 | Bertin |
| 7,172,597 B2 | 2/2007 | Sanford |
| 8,403,935 B2 | 3/2013 | Gross |
| 8,979,847 B2 | 3/2015 | Belcher et al. |
| 2014/0276837 A1* | 9/2014 | Chaney ............... A61B 17/1764 606/88 |
| 2017/0333207 A1* | 11/2017 | Tsukayama .......... A61B 17/155 |

* cited by examiner

*Primary Examiner* — Samuel S Hanna
(74) *Attorney, Agent, or Firm* — Robert J. Hornung

(57) ABSTRACT

An adjustable revision guide for femoral resections comprising a translating stem adaptor, a distal end of the translating stem adaptor configured to selectively attach to a femoral trial/resection guide. The translating stem adaptor configured to selectively translate the femoral trial/resection guide proximally-distally. A proximal end of the translating stem adaptor configured to selectively attach to an offset adaptor of an intramedullary rod. The translating stem adaptor configured to allow for selective locking of rotation of the offset adapter on the translating stem adaptor to thereby lock-in a selected offset. A femoral trial/resection guide selectively attached to the distal end of the translating stem adaptor for use in resecting said distal femur. An intramedullary rod attached to the proximal end of the translating stem adaptor via an offset adaptor on a distal end.

4 Claims, 10 Drawing Sheets

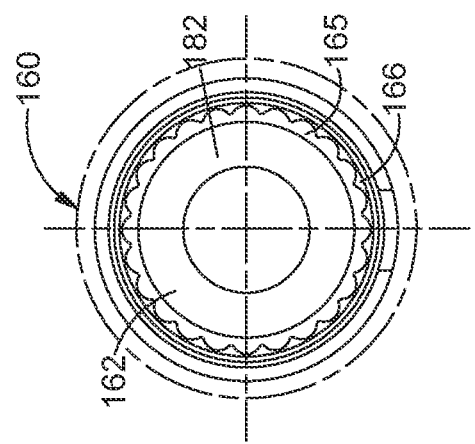
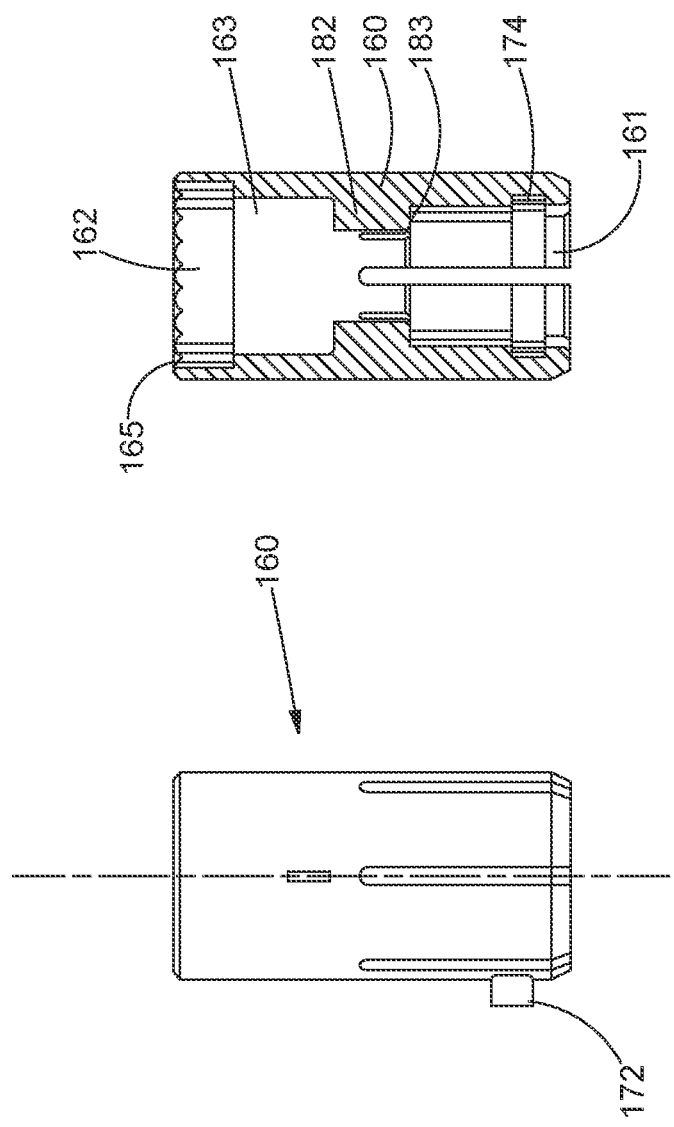
FIGURE 5C
FIGURE 5B
FIGURE 5A

ADJUSTABLE REVISION GUIDE WITH TRANSLATING STEM ADAPTOR

CROSS REFERENCE TO RELATED APPLICATIONS

This application claims the benefit of: U.S. Provisional Patent Application 62/900,499, filed Sep. 14, 2019.

FIELD OF THE INVENTION

The present invention relates to knee arthroplasty, and more particularly to surgical guides for revising the distal femur of a patient undergoing total knee arthroplasty (TKA) or knee revision surgery.

BACKGROUND OF THE INVENTION

Total knee replacement prostheses and instruments are known in the art. In many instances, a specially designed jig or fixture enables the surgeon to make accurate and precise bone resections of the femoral surface in order to accept such prostheses. The ultimate goal with any total knee prosthesis is to approximate the function of the natural, healthy knee structures that the prosthesis is replacing. If the prosthesis is not properly attached to the femur, any misalignment could result in discomfort to the patient, gait problems, or degradation of the prosthesis.

When attaching a knee prosthesis, it is desirable to orient the prosthesis such that the pivot axis of the knee joint lies within a transverse plane that is generally oriented perpendicular to the mechanical axis of the femur. The mechanical axis lies along a line which intersects the femoral head and the center of the ankle. In prior techniques, the mechanical axis had been determined from an inspection of a radiograph of the femur to be resected prior to or during the surgery. During the actual operation, the mechanical axis is determined by computing its valgus angle from the femoral shaft axis. It is then necessary to manually align any cutting guide and its fixtures with respect to the femoral shaft axis in order to achieve an optimum cut.

Often such cutting guides include a femoral intramedullary ("IM") stem or rod that is inserted through a pre-drilled passageway formed in the intercondylar notch and upwardly through the femur along the femoral shaft axis. Such femoral intramedullary stems often include a bracket that supports the distal femur cutting guide, along with features for adjusting the angle of the distal cut. The bracket may include a first pin that extends through the cutting guide to act as a pivot axis. A second pin is attached to the bracket so as to extend through an arcuate slot in the cutting guide. The cutting guide includes pairs of opposing slots formed along its sides which are oriented so as to be perpendicular to a central axis of symmetry of the cutting guide. When the cutting guide is pivoted such that the central axis of symmetry lies along the mechanical axis so as to form the appropriate angle with the femoral shaft axis, the cutting guide slots are positioned to be perpendicular to the mechanical axis. The cutting guide is then locked into the predetermined angle with the femoral shaft axis, and resection of the distal femur may proceed.

Many examples of devices and methods may be found in the art for preparing the distal femur for total knee arthroplasty, such as U.S. Pat. No. 7,172,597 which discloses a provisional component for use with differently sized first and second prosthetic orthopedic components. The provisional component has a configuration that is substantially similar to the first prosthetic component and has a predefined correspondence to the second prosthetic component. The provisional component is mounted on a bone to assess the fit of the first prosthetic component. The provisional component includes a referencing element for defining a reference point on the bone if the fit of the provisional component indicates that the second prosthetic component should be used. An instrument guide is aligned with the reference point and used to properly position a surgical instrument to prepare the bone to receive the second prosthetic component. The provisional and prosthetic components may all be femoral components which have an articulating surface defining a single condylar-shaped projection.

U.S. Pat. No. RE39,301, incorporated herein by reference, discloses a method and apparatus for knee replacement surgery in which a femoral provisional component is provided which corresponds to a permanent component to be implanted in a human. It includes structures suitable for establishing the correct fit and position of such a component, prior to its implantation, in relation to the soft tissues of the knee before final resection of the anterior femoral surface. The provisional component further includes a cutting guide for anterior surface resection such that accurate cuts may be made with the provisional component in place. The method involves preparing the distal femoral surface using the femoral intramedullary canal as a constant reference point for posterior and distal cutting guides followed by locating the provisional component by means of a provisional intramedullary stem so that the relationship with the soft tissues of the knee may be accurately established.

U.S. Pat. No. 6,187,010, incorporated herein by reference, discloses bone cutting guides that appear to enable a surgeon to better gauge required resection characteristics. At least a portion of the guide is transparent, thereby enabling the user to optimize cut estimates and to visualize the resection as it is being performed. At least a portion of the outer surface of the body is shaped to interact with another bone or prosthetic element associated with a joint, thereby enabling the device to function both as a trial and as a cutting guide.

U.S. Pat. No. 5,879,393 discloses a posterior stabilized femoral trial apparatus for preparing a patient's femur to receive a posterior stabilized femoral prosthesis. The device includes a trial body with proximal and distal portions, the distal portion having an articulating surface for articulating with a patient's tibial component. A module selected from a kit fits the trial body at the proximal surface. The module includes a rasping surface that extends longitudinally. The trial body includes cutting surfaces at the posterior condyles. The module is removably attachable to the trial body at the proximal surface. During use the surgeon may resect the patient's femur in a revision case using the trial.

U.S. Pat. No. 6,575,980 discloses an instrument for shaping a femur preparatory to implantation of a knee prosthesis. A gap checking device is fixed to the distal end of the patient's femur and referenced to the epicondyles of the femur. The gap checking device includes slots through which a cutting instrument can be passed to shape the femur so that it can receive the femoral component of the prosthesis. One of the slots enables the distal femoral cut to be made. The thickness of the gap checking device is selected so that the distance between the distal femoral cut and the distal surface of the gap checking device plus the thickness of a shim resting on the cut proximal tibia surface is equal to the combined thickness of the tibial and femoral components of the prosthesis. This arrangement apparently enables balancing of the ligaments to be checked before the femoral cuts are made, but while the gap checking device is secured to the femur.

U.S. Pat. No. 5,053,037 discloses femoral instrumentation for long stem surgery, and provides a femoral drill guide with interchangeable femoral collets, a femoral reamer, and a femoral anterior/posterior cutting block with an adaptable anterior femoral ledge. This instrumentation allows all cuts to be made relative to the long stem component of a femoral prosthesis which will fit in the hole formed by the reamer with the collet and cutting block both oriented on the reamer, and all cuts made by the surgeon will be oriented relative to the long stem or spike component of the femoral prosthesis.

With many of the foregoing, except U.S. Pat. No. 6,187,010, it would be common practice to make one or more cuts with a resection guide in place, then move the guide aside in order to view the interface, to ensure that sufficient bone has been removed to facilitate the most ideal cement interface between the resected bone and implant component. This trial-and-error process not only consumes valuable time during the operation, but may lead to the removal of more bone stock than necessary to achieve fixation. During revision arthroplasty, such trial-and-error is complicated owing to the increased number of resected surfaces involved, and the need to ensure that these surfaces and the medullary stem are all properly aligned during the testing of trial implants and the attachment of the final prosthetic device. In the event of a misalignment, the surgeon may choose to use a final implant having a smaller than optimal diameter stem, for example, to take up the slack upon discovering a slight misalignment with respect to the stem and the resected surfaces. As such, none of the forgoing methods or devices have adequately provided surgeons with a way to easily locate resection guides in relation to the patient's body during orthopedic procedures, such as, total knee replacement surgery.

U.S. Pat. No. 8,979,847 (Belcher) describes a method for preparing a femur for receiving a prosthesis using an intramedullary (IM) member in the femur. A femoral trial component is positioned onto a distal end of the femur. The femoral trial component can have an attachment portion, an articulating surface, and cut surfaces thereon. A modular boss assembly is attached to the attachment portion of the femoral trial component. The modular boss assembly has a boss stem that is configured to operably connect to the IM member. A desired contact between the femoral trial component and the distal femur can be confirmed based on the attaching. The femoral trial component can be fixed to the distal femur based on the confirming. The modular boss assembly can be removed from the femoral trial component. A reamer bushing can be coupled relative to the femoral trial component. A cavity can be reamed into the femur using the reamer bushing as a guide. At least one of a modular femoral box trial and a stem adapter can be coupled relative to the femoral trial component. All of the steps including removing the modular boss assembly, coupling the reamer bushing, reaming the cavity and coupling the modular femoral box trial and stem adapter are performed while the femoral trial component remains fixed to the distal femur.

Improvements on the foregoing concepts are found in U.S. Pat. No. 8,403,935 (Gross), also published as U.S. Pat. Nos. 8,828,014, 9,138,248 and 9,668,749, the disclosures of which are incorporated herein by reference. As indicated in the prior art view of FIG. 1, these patents describe an axial height adjustable revision cutting guide in the shape of a final distal femur implant component. In one embodiment, the revision guide includes a rod adapted for intimate contact within an intramedullary canal of a femur following preparation of the canal to receive the rod. The rod includes a threaded passageway extending longitudinally from a distal end, which is accessible when the rod is installed within the canal. A shaped body of the revision cutting guide is adapted for removable attachment to a distal portion of the femur, and includes an outer surface configured to co-act in a joint and at least two bone-cutting guides are defined through the body corresponding to a level of bone resection. A vernier-bolt is rotatably positioned through the shaped body of the revision cutting guide so as to be adjustably received within the threaded passageway thereby providing for movement of the shaped body of the revision cutting guide relative to the distal portion of the femur.

While the foregoing adjustable revision guides have met with commercial success, there is room for improvement. For example, a drawback of U.S. Pat. No. 8,403,935 is that the instrument does not allow for selective locking of rotation of an offset adaptor.

OBJECTS AND SUMMARY OF THE INVENTION

It is an object of the inventions to provide an adjustable revision guide configured to allow for the selective locking of rotation of offset adapters used during trialing. The foregoing objectives are achieved by providing an adjustable revision guide having the features described herein. The foregoing and other objects, features, aspects and advantages of the invention will become more apparent from the following detailed description of the invention when considered in conjunction with the accompanying drawings.

BRIEF DESCRIPTION OF THE DRAWINGS

FIG. 5A is a side view of one embodiment of a piston of a translating stem adaptor of the invention.

FIG. 5B is a cross-section view of one embodiment of a piston of a translating stem adaptor of the invention.

FIG. 5C is a top view of one embodiment of a piston of a translating stem adaptor of the invention, featuring a seat configured to receive an offset stem in a selected orientation.

DETAILED DESCRIPTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 2A:
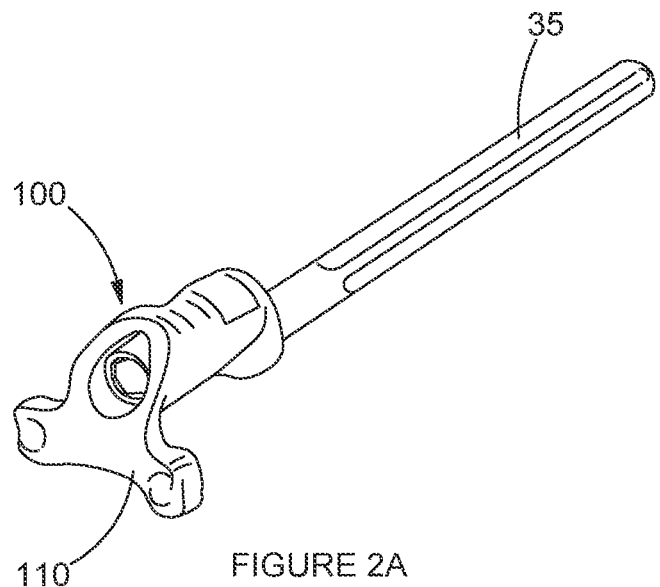
FIG. 2A is a side perspective view of one embodiment of a translating offset stem.
Figure 2B:
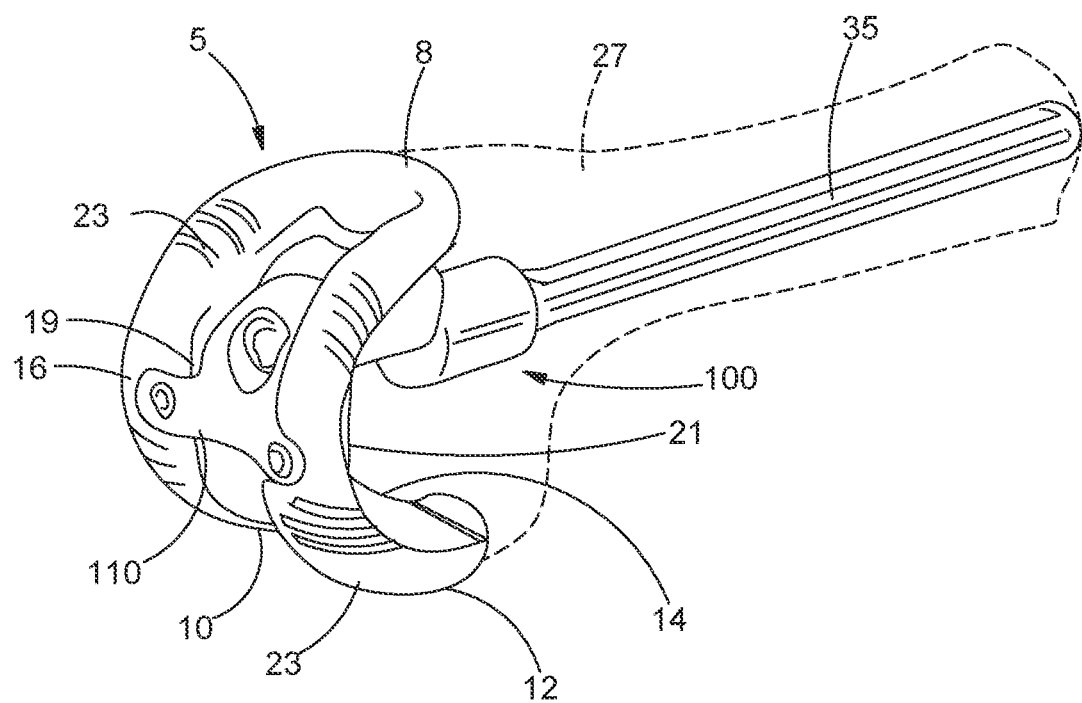
FIG. 2B is a side perspective view of one embodiment of a translating offset stem attached to a resection guide matching a shape of a distal femur.

FIGS. 2A-2B provides a front-side perspective view of one embodiment of a translating stem adaptor 100 of the invention mounted on a combined femoral trial/resection guide 5 (shown in transparent view) and on an attachable intramedullary (IM) rod 35. FIG. 2A is a side perspective view of the translating offset stem 100 disassembled from a femoral resection guide 5. FIG. 2B is a side perspective view of the translating offset stem 100 attached to a resection guide 5 matching a shape of a distal femur. Details about the adjustment features of the translating offset stem 100 will be discussed below.

Figure 1:
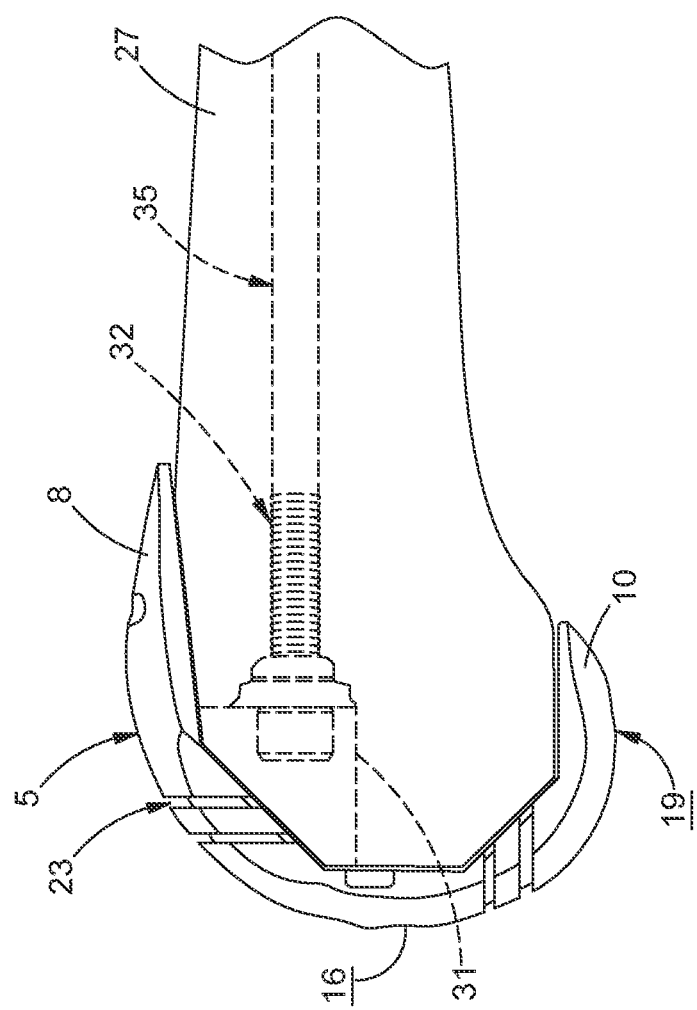
FIG. 1 is a view of a prior art adjustable revision guide.

The femoral trial/resection guide 5 of FIG. 2B generally has the shape of a final femoral knee implant, in a configuration generally known in the art, as shown in the prior art view of FIG. 1. See also U.S. Pat. No. 8,979,847 (Belcher); U.S. Pat. No. 8,403,935 (Gross). However, the translating stem adaptor 100 allows the features of a femoral trial/ resection guide 5 to be used in new and unique ways, as will be described below. The femoral trial/resection guide 5 includes an anterior flange 8, a pair of posterior condylar flanges 10 and 12, and a distal femur contacting surface 14. A distal joint surface 16 corresponds to the natural distal femoral surface of the human knee including condylar surfaces 19 and 21 for cooperation with the corresponding end of a tibia (not shown). Structures for patellar tracking along the arc of the joint surface of the anterior flange 8 and between the distal condylar surfaces 19 and 21 are also provided. One or more resection guide slots 23 are defined in portions of anterior flange 8 and posterior condylar flanges 10 and 12. The guide slots 23 are sized and oriented to accept corresponding saw blades to allow for resection of bone, such as distal and posterior resections, while adjustable trial/cutting guide 5 is positioned on distal femur 27.

Unlike the prior art embodiment of FIG. 1, the present invention is configured to allow for multiple sizes of the femoral trial/resection guide 5 to be selectively attached to a common translating stem adaptor 100, as will be described below. Further, the present invention allows for selective locking of rotation of offset adapters on the IM rod 35. Both of these features reduce system inventory. In addition, the femoral trial/resection guide 5 can be selectively translated proximally-distally.

FIGS. 3A-3C and 4 show one alternative embodiment of a translating stem adaptor 100. The configuration of FIGS. 3A-3C allows the adaptor 100 to be shorter than the adaptor 100 configuration of FIG. 7A-7C, discussed below, which improves accuracy of the trial. FIGS. 2A-2B, discussed above, provide views of the use of the adaptor 100 of FIG. 3A-3C on an IM rod 35 and femoral trial/resection guide 5.

Figure 3A:
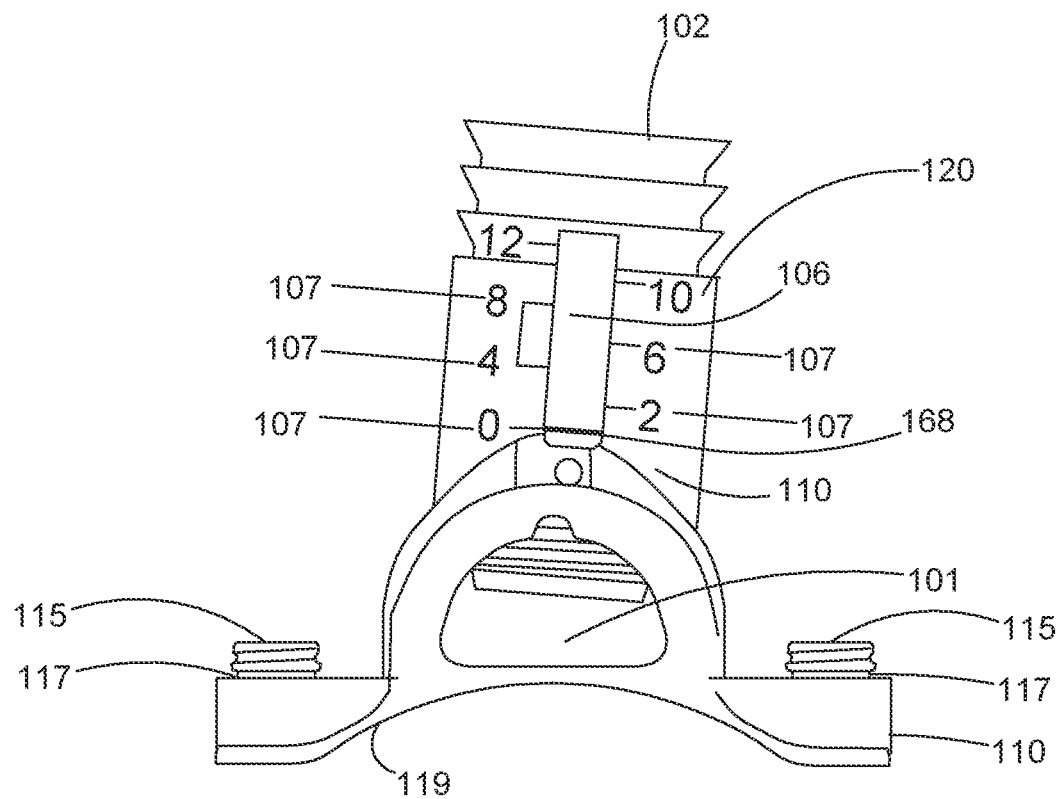
FIG. 3A is a top view of one embodiment of a translating stem adaptor of the invention.
Figure 4:
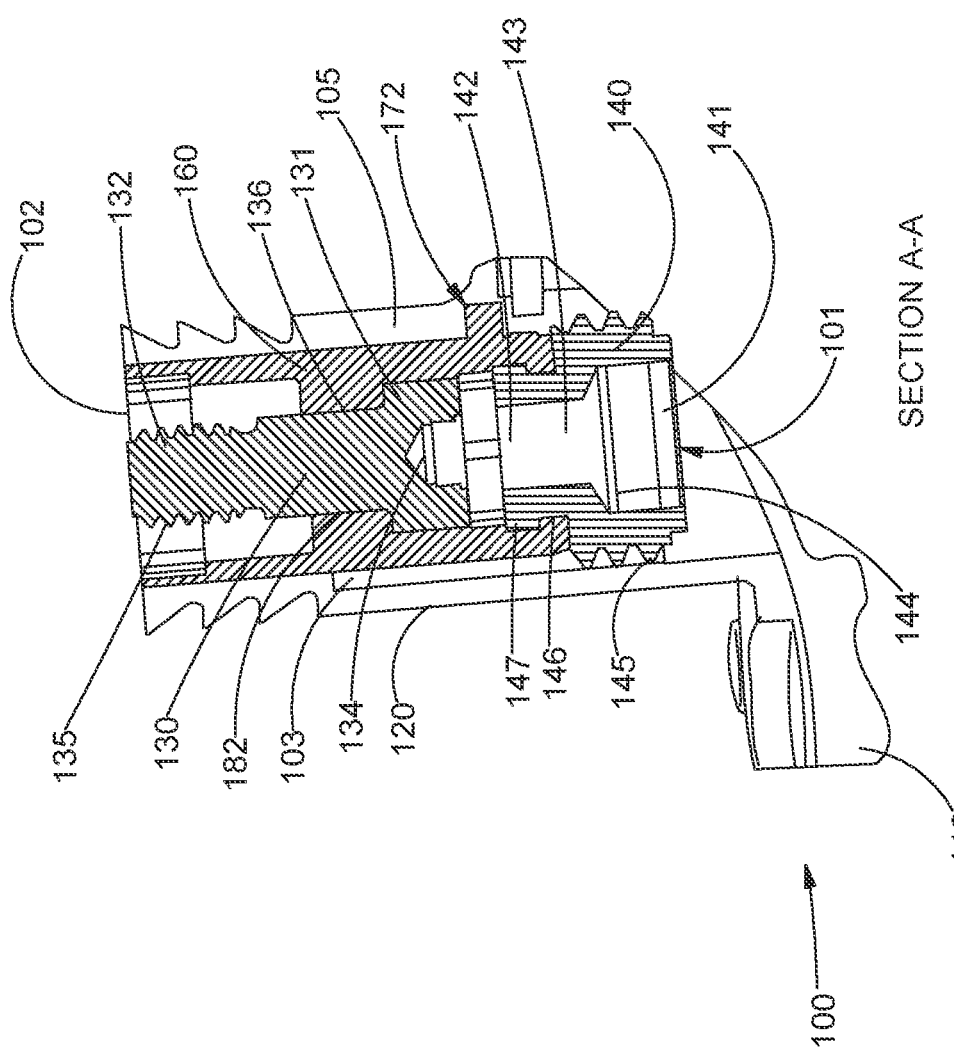
FIG. 4 is a cross-section view showing of one embodiment of a translating stem adaptor of the invention.

As shown in the top view of FIG. 3A, the translating stem adaptor 100 includes, generally, a femoral inset portion 110 and an adaptor housing 120 extending proximally from the femoral insert portion 110. A first open end 101 is formed through the femoral insert portion 110, and a second open end 102 is formed through a proximal end of the adaptor housing 120. A through bore 103 extends between the first and second open ends 101, 102, as can be seen more clearly in FIG. 4. The through bore 103 is configured to receive a translating mechanism, as shown in FIG. 4 and described in further detail herein.

As shown in FIG. 3A, a patellar groove/intercondylar notch 119 is formed along a distal front of the translating stem adaptor 100 adjacent the first open end 101, to generally match the patellar groove/intercondylar notch of a natural femur and of a femoral trial/resection guide 5. A sizing window 106 is formed through the adaptor housing 120 for using in viewing a marker 108 on the outer surface of the piston 160. A plurality of size markings 107, such as in millimeter increments are provided on the adaptor housing 120 along the sizing window 106. As will be described below, the size markings are used to determine the amount of proximal/distal translation of the femoral trial/resection guide 5 relative to the IM rod 35.

Figure 3B:
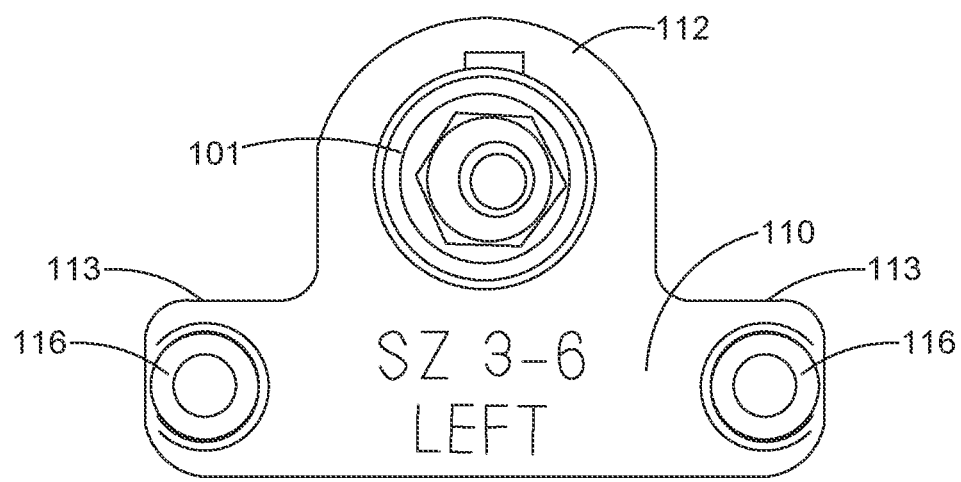
FIG. 3B is a front view of one embodiment of a translating stem adaptor of the invention.

As shown in FIGS. 3A and 3B, the translating stem adaptor 100 includes a femoral insert portion 110 on a distal end thereof. The femoral insert portion 110 is configured to fit into a matching opening in the intercondylar notch of the femoral trial/resection guide 5, such that multiple sizes of femoral trial/resection guides 5 can be selectively attached to and removed from the translating stem adaptor 100. The insert portion 110 includes a base portion 112. Opposing wing members 113 extend from the base portion 112. Each wing member 113 is provided with an attachment member 115. In the embodiment of FIG. 3A-3B, the attachment member is a captured screw 115 on each of the wing members 113. A thread 117 of the captured screw 115 is positioned to engage a matching threaded bore on the femoral trial/resection guide 5. A drive portion 116 of the screw 115 is readily accessible from the distal end of the translating stem adaptor 100 for use in securing the screw 115 in the matching threaded bore on the femoral trial/ resection guide 5.

Figure 3C:
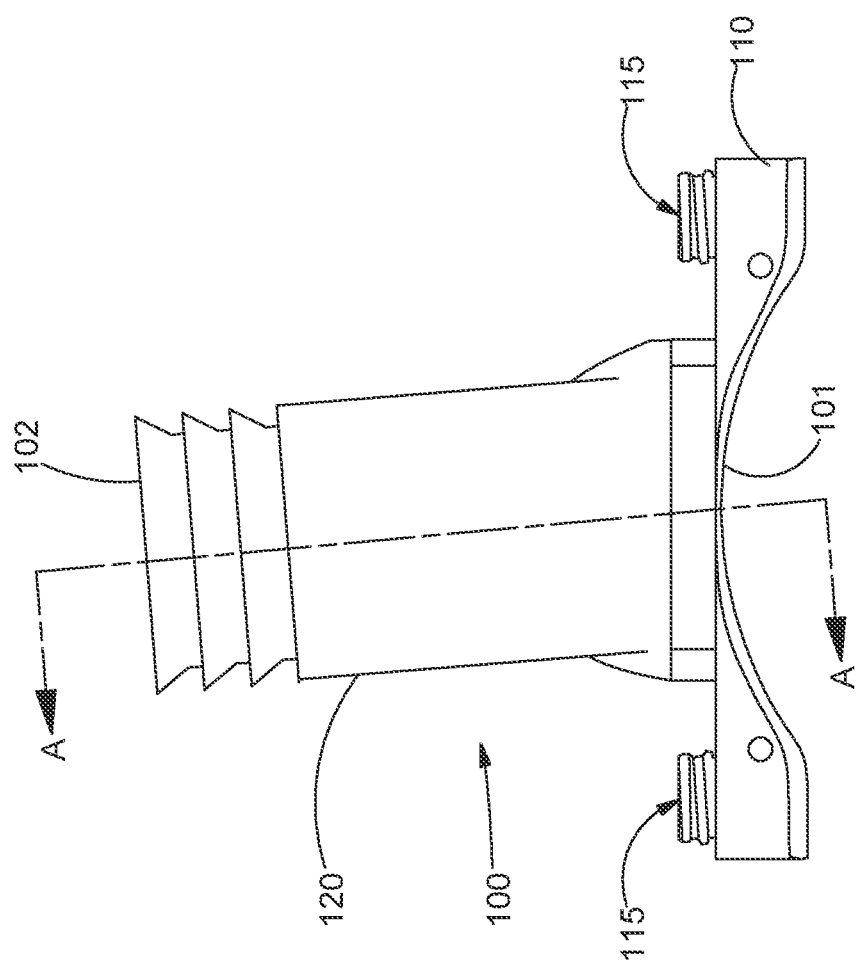
FIG. 3C is a bottom view of one embodiment of a translating stem adaptor of the invention.

FIG. 3C shows a bottom view of the translating stem adaptor 100. FIG. 4 is a cross-section view taken along A-A of FIG. 3C showing an internal arrangement of the translating stem adaptor 100. Additional details of the piston 160 are shown in FIGS. 5A-5C. A stem gear 140, piston 160 and pass through screw 130 are arranged in the though bore of the adaptor housing 120.

The stem gear 140 includes a first open end 141, a second open end 142 and a through bore 143 extending between the first and second open ends 141, 142. A drive engagement member 144 is provided along the first open end 141. A thread 145 is provided on an exterior surface extending proximally from the first open end 141. The thread 145 engages a matching thread on the interior wall of the adaptor housing 120 for use in selectively translating the stem gear 140 proximally-distally within the adaptor housing 120. An annular ring 147 and undercut 146 are formed along the proximal end of the stem gear 140. The annular ring 147 and undercut 146 allow the stem gear to be rotatably captured in a distal end of the piston 160. Thus, translation of the stem gear 140 simultaneously translates the piston 160 within the adaptor housing 120.

The pass through screw 130 includes a head 131, and a shaft 132 having a smooth portion and a thread 135 on a proximal or leading portion. The head 131 has a drive engagement member 134, such as a hex drive. As can be seen, the head 131 of the pass through screw 130 is captured in an interior cavity bordered on a proximal end by a centralized annular protrusion 182. When the thread 135 is engaged in a matching threaded bore of the offset connector 190, the pass through screw 130 serves to lock the offset connector 190 to the piston 160. Thus, when the stem gear 140 translates the piston 160, it simultaneously translates the IM rod 35. The offset connector 190/IM rod 5 assembly can be selectively unlocked from the piston 160 simply by reversing the pass through screw 130 to disengage the internal threads of the offset connector 190.

FIG. 5A is a side view of one embodiment of a piston 160 of a translating stem adaptor 100 of the invention. The piston 160 has a smooth annular outer wall. Slots are provided along the first end for use in seating the stem gear 140 in a captured relationship in the stem gear groove 174. The piston 160 includes an orientation peg 172 for engaging the body 105 of the translating stem adaptor 100 to prevent rotation of the piston 160 relative to the body 105.

FIG. 5B is a cross-section view of the piston 160. The piston 160 includes an open first end 161, an open second end 162, and a through bore 163 extending between the first and second ends 161, 162. Various support structures are formed in the through bore 163 for facilitating the function of the translating stem adaptor 100. A stem gear groove 174 is formed on the interior wall of the through bore 163 in the area of the first open end 161. The stem gear groove 174 is an annular groove that captures the annular ring 147 of the distal end of the stem gear 140 in a rotating relationship. A generally centralized annular protrusion 182 along the interior wall of the through bore 163 provides a seat 183 for a head of the pass through screw 130.

FIG. 5C shows details of a proximal end of the piston 160, where the piston engages the offset base portion 193 of the IM rod 35. An annular rod seat 165 is formed along the interior wall of the second or proximal open end 162 of the piston body 160. The rod seat 165 provides a stop position for a shoulder 197 of the offset connector 190. A plurality of teeth 166 are formed on the interior wall of the piston 160 along the proximal open end 162 for use in engaging matching teeth 196 of the offset connector 190.

Figure 6:
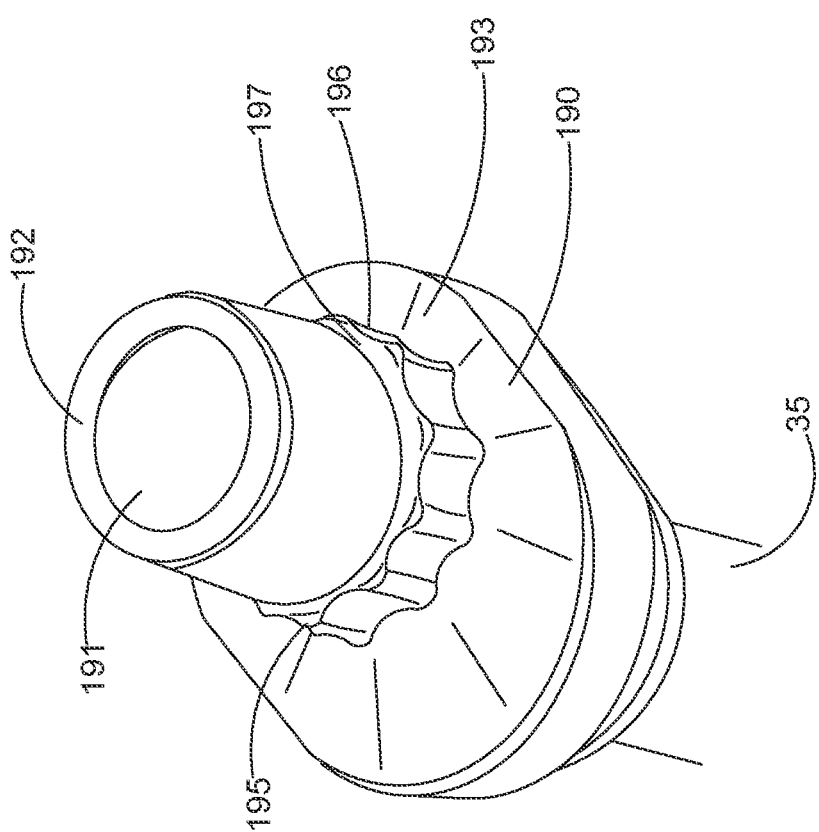
FIG. 6 is a top perspective view of one embodiment of an offset stem featuring a shoulder configured for engagement in a seat of a piston for securement in a selected orientation.

FIG. 6 is a top perspective view of one embodiment of an offset stem/IM rod 35/offset connector 190 assembly configured for use with the translating stem adaptor 100. The stem 35 includes a conventional IM rod portion 35. A distal end of the stem 35 has an offset connector 190. The offset connector 190 is in a fixed relationship to the stem 35. The offset connector 190 includes an offset base portion 193 having a general ovoid or other lengthwise shape. An adaptor insert portion 192 extends distally from the offset base portion 193. The axis of adaptor insert portion 192 is offset from the axis of the rod 35. The adaptor insert portion 192 is configured to closely fit the rod seat 165 of the piston 160. The adaptor insert portion 192 has a bore 191 configured to receive the pass through screw 130. An interior thread in the adaptor insert bore 191 matches the thread 135 of the pass through screw 130 for use in selectively locking the offset stem 35 to the translating stem adaptor 100.

An orientation feature 195 is provided on the offset connector 190. In the embodiment of FIG. 6, the orientation feature 195 comprises a collar 195 formed from a plurality of rod teeth 196. The collar 195 is formed on a lower end of the adaptor insert portion 192, adjacent the offset base portion 193. The rod teeth 196 are sized and configured to match and interdigitate with the piston teeth 166 formed in the seat 165 of the piston 160. The collar teeth 196 and piston teeth 166 are together configured to provide discrete positions of offset between the rod 35 and the translating stem adaptor 100, such as twelve discrete orientations. This arrangement allows the rod 35 can be selectively placed in a selected offset position relative to the translating stem adaptor 100. The collar 195 includes a shoulder 197. When the offset connector 190 is maximally threaded onto the pass through screw 130, the shoulder 197 abuts against the rod seat 165 of the piston 160. Together, the foregoing features lock the rod 35 in a selected offset position from the translating stem adaptor 100 for use in revision knee procedures.

Figure 7A:
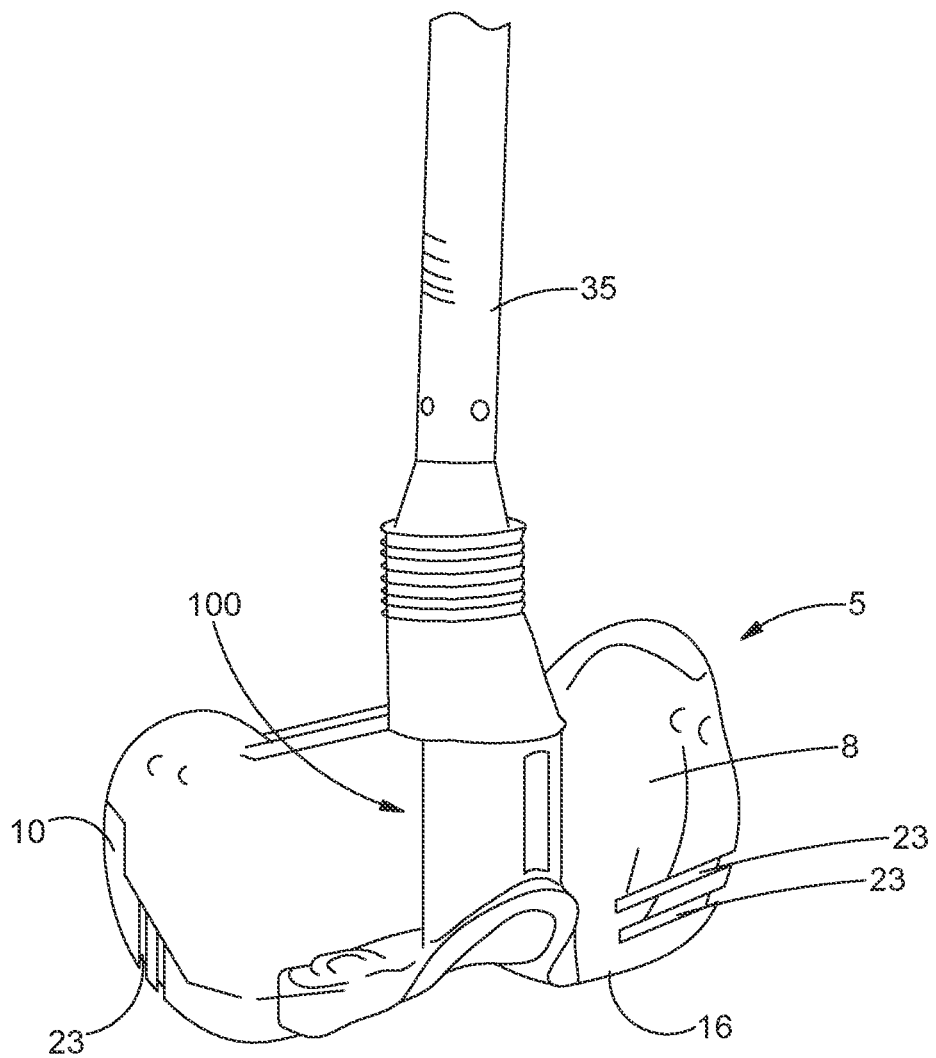
FIG. 7A is a front-side perspective view of one embodiment of a translating stem adaptor of the invention mounted on a femoral trial/resection guide and an intramedullary (IM) rod, showing the translating stem adaptor in a maximally retracted position.
Figure 7B:
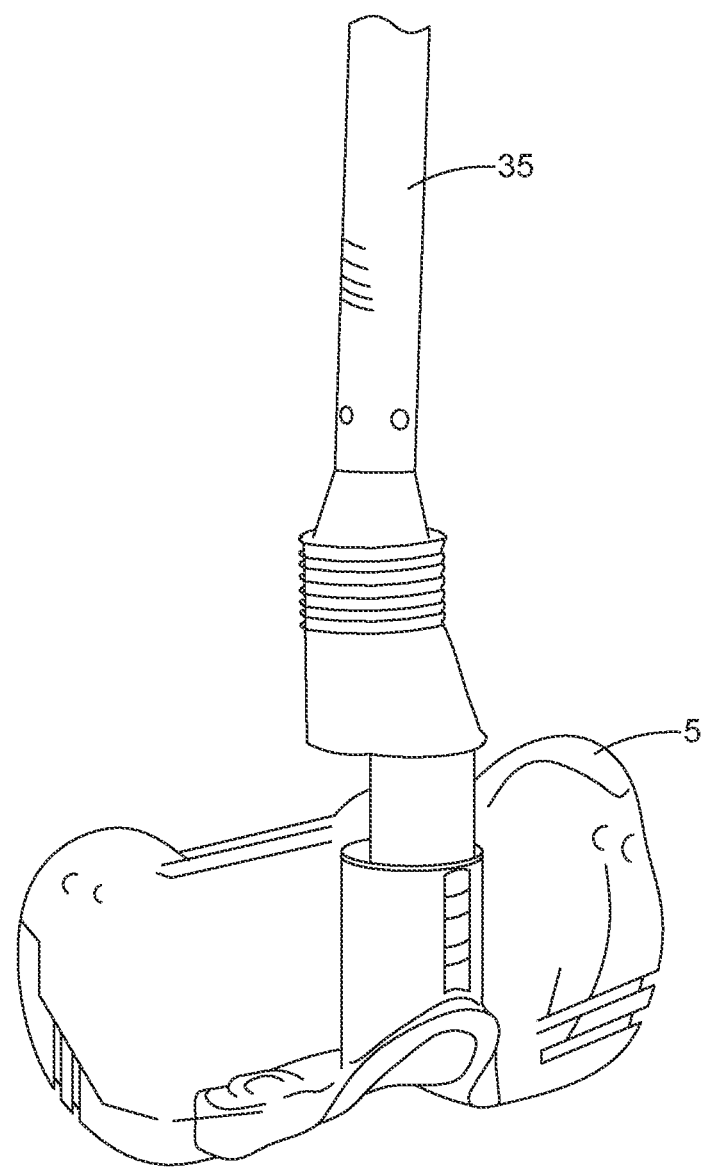
FIG. 7B is a front-side perspective view of one embodiment of a translating stem adaptor of the invention mounted on a femoral trial/resection guide and an intramedullary (IM) rod, showing the translating stem adaptor in an extended position.

FIGS. 7A-7B provides a front-side perspective view of an alternative embodiment of a translating stem adaptor 100 of the invention mounted on a combined femoral trial/resection guide 5 (shown in transparent view) and on an attachable intramedullary (IM) rod 35. FIG. 7A shows the translating stem adaptor 100 in a maximally retracted position. FIG. 7B is similar to FIG. 7A but shows the translating stem adaptor 100 in an extended position.

The femoral trial/resection guide 5 of FIG. 7A-7B generally has the shape of a final femoral knee implant, in a configuration generally known in the art, as shown in the prior art view of FIG. 1. The femoral trial/resection guide 5 includes an anterior flange 8, a pair of posterior condylar flanges 10 and 12, and a distal femur contacting surface 14. A distal joint surface 16 corresponds to the natural distal femoral surface of the human knee including condylar surfaces 19 and 21 for cooperation with the corresponding end of a tibia (not shown). Structures for patellar tracking along the arc of the joint surface of the anterior flange 8 and between the distal condylar surfaces 19 and 21 are also provided. One or more resection guide slots 23 are defined in portions of anterior flange 8 and posterior condylar flanges 10 and 12. The guide slots 23 are sized and oriented to accept corresponding saw blades to allow for resection of bone, such as distal and posterior resections, while adjustable trial/cutting guide 5 is positioned on distal femur 27.

Unlike the prior art embodiment of FIG. 1, the present invention is configured to allow for multiple sizes of the femoral trial/resection guide 5 to be selectively attached to a common translating stem adaptor 100, as will be described below. Further, the present invention allows for selective locking of rotation of offset adapters on the IM rod 35. Both of these features reduce system inventory. In addition, the femoral trial/resection guide 5 can be selectively translated proximally-distally.

Figure 7C:
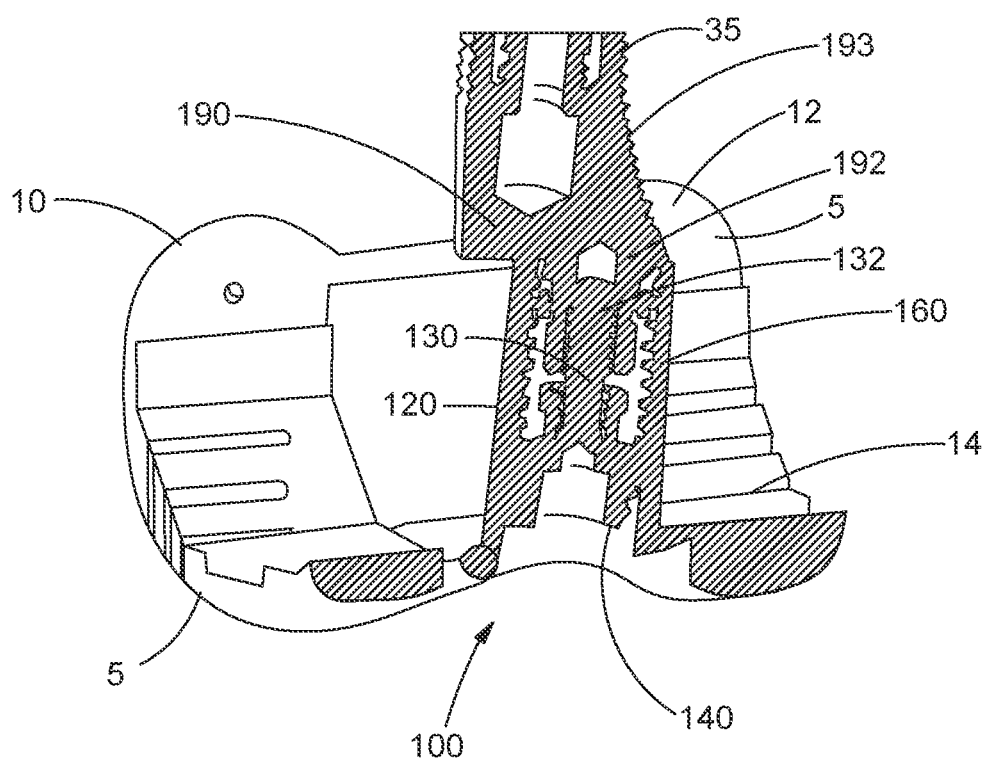
FIG. 7C is a cross-section view of one embodiment of a translating stem adaptor of the invention mounted on a femoral trial/resection guide and an intramedullary (IM) rod, showing details of one embodiment of a translation mechanism.

FIG. 7C provides a cross-section view of one embodiment of a translating stem adaptor 100 of the invention mounted on a femoral trial/resection guide and an intramedullary (IM) rod, showing details of one embodiment of a translation mechanism. The translating stem adapter 100 has a fixed angle of 5° from the femoral mechanical axis. This angulation can also be seen in in FIG. 3A. The translation mechanism includes, generally, a stem gear 140, a pass through screw 130, and a piston 160 in a housing 120 of the translating stem adaptor 100. An IM rod 35 is attached to the translating stem adaptor 100 via an offset connector 190. The offset connector 190 includes an offset base portion 193 having an adaptor insert portion 192. The axis of the insert portion 192 is offset from the axis of the IM rod 35. This offset arrangement allows the rod 35 to be selectively set at various offset positions relative to the femoral trial/resection guide 5. The pass through screw 130 serves to lock the piston 160 of the translating stem adaptor housing 100 to the offset connector 190 by engaging internal threads on the adapter insert portion 192, thus locking the rod 35 in a selected offset position. With the IM rod 35 locked on the piston 160, the surgeon uses a driver to rotate the stem gear 140 to selectively translate the piston 160 proximally-distally within the adaptor housing 120, and in turn translate the proximal-distal position of the femoral trial/resection guide 5 relative to the IM rod 35.

The present invention solves many of the problems in the art by providing an axial height adjustable as well as selective locking of rotation of offset adapters to a revision cutting guide in the shape of a final distal femur implant component, thereby ensuring that once the guide is removed, the final implant component will inherently match the executed resections. This saves considerable time while improving accuracy.

During a total knee replacement procedure, the present invention provides a trial component that offers the surgeon the ability to perform flexion trials as well as resection procedures without the need to remove the trial prosthesis from the distal femur. The structural arrangement of the adjustable trial/cutting guide 5 enables it to be placed in the joint space following initial resection of the distal and posterior femur. The amount of resection of the posterior and distal surfaces of the medial and lateral condyles is preferably kept to a minimum. Each condyle is preferably resected independently of the other, and separate augments are selected for test fitting the adjustable trial/cutting guide 5 and for implantation of the final femoral implant component. The initial cuts may be standardized for a typical range of knee sizes or the cuts may be made on an individual basis according to the needs of the particular patient.

Methods

Methods of using the foregoing instruments in knee revision procedures will now be described.

Using any of various known revision knee techniques, the proximal tibia and distal femur are resected to accommodate a tibial trial and the femoral trial/resection guide 5. In prior steps in the revision procedure, a longitudinally extending pre-drilled IM canal will typically have been formed in the intercondylar notch and upwardly through the femur along the femoral shaft axis. The drilled IM canal will typically include an opening formed in the femur at the distal most end of the canal for receiving the translating stem adaptor 100 and the offset connector 190. The IM canal will be used to accommodate the intramedullary rod 35 of the translating stem adaptor 100/offset connector 190 instrument construct, as described below.

The flexion/extension gap is assessed. The flexion/extension gap can be assessed by pinning the cut-through femoral trial 5 using threaded headed pins through the anterior pin holes. The surgeon removes previously installed hardware (e.g. fixed reamer, offset bushing, and valgus bushing). An appropriate tibial insert trial is inserted on the previously prepared trial tibial base. The surgeon assesses the flexion and extension gaps using conventional techniques. The function of the patient's knee is checked as well as the relationship of the adjustable trial/cutting guide 5 to the soft tissues of the joint.

An appropriately sized translating trial stem or translating offset trial stem 190 is assembled to the translating stem adapter 100. If using an offset stem 190, ensure that the offset is set to the previously determined rotation using the laser marking on the medial side of the translating stem adapter 100. The adaptor insert portion 192 is oriented for insertion into the proximal open end 162 of the piston 160.

The open proximal end 162 of the piston 160 is placed onto the adaptor insert portion 192. The surgeon uses a driver (such as a 3.5 mm driver) to rotate the pass-through screw 130 to engage the interior thread of the adaptor insert portion 192 of the offset connector 190. With the piston teeth 166 and rod teeth engaged in a desired offset orientation, the pass-through screw 130 is tightened to lock the translating stem adaptor 100 to the IM rod/offset connector 190.

Splined cones are used for fixation of the translating stem adaptor 100/offset connector 190 construct. The use of a splined cone requires additional preparation of the distal femoral canal. The size of the splined cone and a secondary reamer are determined, such as based on the diameter of the primary or fixed reamer. Using the appropriate secondary reamer, ream approximately one inch into the distal femoral canal.

The cut-through femoral trial 5 is removed and connected to the translating stem adaptor 100/offset connector 190 construct. The captured screws 115 on the translating stem adapter construct 100 are aligned with the screw holes on the cut-through femoral trial 5. Tighten the two screws 115 on the cut through bushing adapter 110 with a driver (e.g. 3.5 mm driver) to lock the translating stem adaptor 100 on the femoral trial/resection guide 5. The appropriate splined cone is assembled on the translating stem trial by sliding the splined cone up the stem 35 toward the cut-through femoral trial 5 until the splined cone snaps into place.

The femoral trial/resection guide 5/translating stem adaptor 100/offset connector 190 assembly is placed on the resected distal femur. The IM rod 35 is placed in the pre-drilled IM canal. Once in position on the femur, the surgeon uses a driver to rotate the stem gear 140. As described above, the stem gear 140 translates the adjustable trial/cutting guide 5 proximally-distally relative to the intramedullary rod 35. The adjustable trial/cutting guide 5 may be moved toward or away from the distal femur, generally parallel with the mechanical axis of femur, by clockwise or counter clockwise rotation of the stem gear 140. The use of a screw mechanism allows for continuous rather than discrete adjustments. Small longitudinal adjustments may be made in the position of adjustable trial/cutting guide 5 relative to the femur 27. Trial flexions and extensions of the joint may be made, with adjustments to the axial position of the adjustable trial/cutting guide 5 on the distal femur 27 being made via the engagement of the stem gear 140 in the translating stem adaptor 100.

Once correct working of the joint is established, including balancing of the soft tissues, anterior and distal augment resections may be accomplished through the cutting guides 23 without removing the adjustable trial/cutting guide 5, thereby ensuring that these cuts are made in the correct locations relative to the intramedullary canal and at the correct angles relative to the intramedullary stem 35. Because the system of revision for which adjustable trial/cutting guide 5 is intended uses the intramedullary canal of the femur as a reference point, the angle established between the intramedullary shaft and the anterior flange of an implant is constant through all sizes of such implants.

Although the size of the femoral prosthesis, and thus of the adjustable trial/cutting guide 5, is determined before surgery, it may be necessary, following the initial resection, to adjust to an alternative size component in order to tighten the flexion and extension gaps. The present invention facilitates this process by permitting the sizes to be tested and the distal femur to be further resected, as needed, before the final prosthesis is implanted. The translating stem adaptor 100 facilitates sizing by allowing the femoral trial/resection guide 5 to be removed from the translating stem adaptor 100 and replaced with a different size. In order to remove the femoral trial/resection guide 5, the entire construct is pulled from the patient, the two screws 115 of the translating stem adaptor 100 are undone to release the femoral trial/resection guide 5, and then the translating stem adapter 100 is attached to the next size trial.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. An instrument for use as an adjustable revision guide for femoral resections in total knee arthroplasty procedures on a distal femur of a knee of a patient comprising:
   a translating stem adaptor, wherein the translating stem adaptor comprises:
      a distal end of the translating stem adaptor configured to selectively attach to a femoral trial or resection guide selected from multiple sizes of femoral trials or resection guides,
      a femoral insert portion on the distal end of the translating stem adaptor,
         whereby the multiple sizes of femoral trials or resection guides may be selectively attached to the translating stem adaptor,
         the translating stem adaptor configured to selectively translate the femoral trial or resection guide proximally-distally,
      a proximal end of the translating stem adaptor configured to selectively attach to an offset connector of an intramedullary rod,
         the translating stem adaptor configured to allow for selective locking of rotation of the translating stem adaptor relative to the offset connector of the intramedullary rod to thereby lock-in a selected offset position,
      an adaptor housing extending to the proximal end of the translating stem adaptor from the femoral insert portion, the adaptor housing having:
         a first open end formed through the femoral insert portion,
         a second open end formed through the proximal end of the translating stem adaptor, and
         a through bore extending between the first open end and the second open end,
            wherein a piston is disposed in the though bore of the adaptor housing,
            wherein a stem gear is arranged in the first open end of the adaptor housing for use in selectively translating the femoral trial or resection guide proximally-distally, the stem gear being rotatably affixed to the piston, and
               wherein the stem gear includes:
                  a stem gear first open end,
                  a stem gear second open end, and
                  a stem gear through bore extending between the stem gear first open end and the steam gear second open end,
                  a drive engagement member provided along the stem gear first open end for use in rotating the stem gear, the stem gear through bore providing access to a head of a pass through screw for use in rotating the pass through screw;
   a femoral trial or resection guide selectively attached to the distal end of the translating stem adaptor for use in resecting said distal femur; and
   an intramedullary rod attached to the proximal end of the translating stem adaptor via the offset connector, the offset connector having an adaptor insert portion extending distally from an offset base portion,
      the adaptor insert portion having an axis that is offset from an axis of the intramedullary rod,
   wherein the pass through screw is disposed in a proximal portion of the piston for use in engaging the offset connector for selectively locking rotation of the translating stem adaptor relative to the offset connector of the intramedullary rod,
   wherein the adaptor insert portion of the offset connector is configured to closely fit in a rod seat of the piston, the adaptor insert portion having a bore configured to receive the pass through screw, an interior thread in bore of the adaptor insert portion matching a thread of the pass through screw for use in selectively locking the offset connector to the translating stem adaptor,
   wherein the offset connector includes the offset base portion having a lengthwise shape,
   wherein the offset connector has an orientation feature comprising a collar formed from a plurality of collar teeth, the collar formed on a lower end of the adaptor insert portion adjacent the offset base portion, and
   wherein the plurality of collar teeth are sized and configured to match and interdigitate with a plurality of piston teeth formed in the rod seat of the piston, the collar teeth and the piston teeth together configured to provide discrete positions of offset between the intramedullary rod and the translating stem adaptor to thereby allow the intramedullary rod to be selectively placed in the selected offset position relative to the translating stem adaptor.

2. The instrument of claim 1, wherein the discrete positions of offset between the intramedullary rod and the translating stem adaptor include twelve discrete orientations.

3. The instrument of claim 1, wherein the translating stem adapter is angled at a fixed angle from a femoral mechanical axis.

4. The instrument of claim 3, wherein the fixed angle is 5 degrees.

* * * * *